(12) United States Patent
Wunsch et al.

(10) Patent No.: US 11,094,683 B2
(45) Date of Patent: Aug. 17, 2021

(54) BONDED NANOFLUIDIC DEVICE CHIP STACKS

(71) Applicant: INTERNATIONAL BUSINESS MACHINES CORPORATION, Armonk, NY (US)

(72) Inventors: Benjamin Wunsch, Mt. Kisco, NY (US); Joshua T. Smith, Croton on Hudson, NY (US); Stacey Gifford, Fairfield, CT (US); Michael Albert Pereira, Westchester, NY (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 77 days.

(21) Appl. No.: 16/364,649

(22) Filed: Mar. 26, 2019

(65) Prior Publication Data

US 2020/0312834 A1 Oct. 1, 2020

(51) Int. Cl.
*H01L 25/00* (2006.01)
*H01L 23/00* (2006.01)
*H01L 25/065* (2006.01)
*H01L 25/04* (2014.01)
*G01N 33/487* (2006.01)
*G01N 33/50* (2006.01)

(52) U.S. Cl.
CPC ....... *H01L 25/50* (2013.01); *G01N 33/48707* (2013.01); *G01N 33/50* (2013.01); *H01L 24/05* (2013.01); *H01L 24/94* (2013.01); *H01L 25/042* (2013.01); *H01L 25/0657* (2013.01); *H01L 2224/05* (2013.01); *H01L 2224/94* (2013.01); *H01L 2924/06* (2013.01); *H01L 2924/10253* (2013.01)

(58) Field of Classification Search
None
See application file for complete search history.

(56) References Cited

U.S. PATENT DOCUMENTS

| 7,683,459 | B2 | 3/2010 | Ma et al. |
| 8,871,549 | B2 | 10/2014 | Ellis-Monaghan et al. |
| 9,314,764 | B2 | 4/2016 | Hess et al. |
| 9,651,542 | B2 | 5/2017 | Yu et al. |
| 9,714,933 | B2 | 7/2017 | Harrer et al. |
| 10,006,899 | B2 | 6/2018 | Tian |
| 2008/0150125 | A1* | 6/2008 | Braunisch ........... H01L 25/0657 257/712 |

(Continued)

*Primary Examiner* — Nilufa Rahim
(74) *Attorney, Agent, or Firm* — Cantor Colburn LLP; Kristofer Haggerty

(57) ABSTRACT

A method of producing a bonded chip stack is described. A first nanofluidic device chip having a first through-wafer via is formed. A second nanofluidic device chip having a second through-wafer via is formed. The first nanofluidic device chip and the second nanofluidic device chip are washed with a detergent solution. A first surface of the first nanofluidic device chip and a second surface of the second nanofluidic device chip are activated by treating the first surface and the second surface with an activation solution. The first nanofluidic device chip and the second nanofluidic device chip are arranged in a stack. The first through-wafer via is aligned with the second through-wafer via in a substantially straight line. The stack of first and second nanofluidic device chips is subjected to annealing conditions.

19 Claims, 8 Drawing Sheets

(56) References Cited

U.S. PATENT DOCUMENTS

| | | |
|---|---|---|
| 2010/0225002 A1* | 9/2010 | Law ................. H01L 21/76898 257/774 |
| 2010/0248209 A1 | 9/2010 | Datta et al. |
| 2012/0193235 A1 | 8/2012 | Afzali-Ardakani et al. |
| 2016/0172324 A1* | 6/2016 | Kuczynski ........... B23K 1/0016 228/9 |
| 2017/0194248 A1* | 7/2017 | Das ....................... H01L 23/528 |
| 2018/0070869 A1 | 3/2018 | Ionescu et al. |
| 2018/0259475 A1 | 9/2018 | Xiao et al. |
| 2020/0013699 A1* | 1/2020 | Liu ........................ H01L 24/08 |

\* cited by examiner

1102 — FABRICATE NANOFLUIDIC DEVICE CHIPS USING SI NANOFABRICATION

1104 — RINSE THE CHIPS WITH ORGANIC SOLVENT

1106 — WASH THE CHIPS WITH AQUEOUS DETERGENT SOLUTION

1108 — RINSE WITH DEIONIZED WATER

1110 — ACTIVATE BY TREATING WITH AN ACTIVATING SOLUTION

1112 — STACK THE CHIPS USING AN ALIGNMENT JIG

1114 — SUBJECT THE STACK TO ANNEALING CONDITIONS

FIG. 11

1202 — FABRICATE NANOFLUIDIC DEVICE CHIPS USING SILICON NANOFABRICATION

1204 — FORM A LAYER OF SILICON OXIDE

1206 — IMPLANT A BORON LAYER ON THE SILICON OXIDE LAYER

1208 — WASH WITH AN AQUEOUS DETERGENT SOLUTION

1210 — FORM A STACK OF CHIPS USING AN ALIGNMENT JIG

1214 — APPLY ELECTRIC CURRENT TO THE STACK

FIG. 12

# BONDED NANOFLUIDIC DEVICE CHIP STACKS

BACKGROUND

The present invention relates in general to nanofluidic chips. More specifically, the present invention relates to fabrication methods and resulting structures for bonded nanofluidic chip stacks containing through-wafer vias that allow fluids to be transported between chip layers for high-throughput nanofluidics.

Nanofluidics is study of the behavior, manipulation, and control of fluids that are confined to nanometer structures having characteristic dimensions that are typically 1-100 nanometers (nm). Fluids confined in these nanometer structures exhibit physical behaviors not observed in larger structures, such as those of micrometer dimensions and above, because the characteristic physical scaling lengths of the fluid (e.g., Debye length, hydrodynamic radius) very closely coincide with the dimensions of the nanostructure itself. In nanofluidics, fluids are moved, mixed, separated, or otherwise processed. Numerous applications employ passive fluid control techniques like capillary forces. In some applications external actuation means are additionally used for a directed transport of the fluids.

SUMMARY

Embodiments of the present invention are directed to a method of forming a bonded chip stack. A non-limiting example of the method includes forming a first nanofluidic device chip having a first through-wafer via, and forming a second nanofluidic device chip having a second through-wafer via. The first nanofluidic device chip and the second nanofluidic device chip are washed with a detergent solution, and a first surface of the first nanofluidic device chip and a second surface of the second nanofluidic device chip are activated by treating the first surface and the second surface with an activation solution. The first nanofluidic device chip and the second nanofluidic device chip are arranged in a stack, wherein the first through-wafer via is aligned with the second through-wafer via in a substantially straight line. The stack of first and second nanofluidic device chips is subjected to annealing conditions.

Embodiments of the present invention are directed to a method of producing a bonded chip stack including at least two nanofluidic device chips. The method includes providing at least two nanofluidic device chips wherein each nanofluidic device chip includes at least one through-wafer via, forming a silicon oxide layer on the surface of each nanofluidic device chip, implanting a boron layer on the silicon oxide layer, washing the nanofluidic device chips with a detergent solution, arranging the nanofluidic device chips in a stack wherein the through-wafer vias of each nanofluidic device chip are aligned in a straight line, and applying an electrical voltage to the stack of nanofluidic device chips.

Embodiments of the present invention are directed to a stack of bonded nanofluidic device chips. The stack of bonded nanofluidic chips includes at least two nanofluidic device chips, wherein each nanofluidic device chip includes at least one through-wafer via, the through-wafer vias of the nanofluidic device chips are aligned in a straight line, and the nanofluidic chips are bonded to each other by thermal annealing or anodic bonding.

Additional technical features and benefits are realized through the techniques of the present invention. Embodiments and aspects of the invention are described in detail herein and are considered a part of the claimed subject matter. For a better understanding, refer to the detailed description and to the drawings.

BRIEF DESCRIPTION OF THE DRAWINGS

FIG. 11 depicts a flow diagram illustrating a methodology according to one or more embodiments of the invention; and FIG. 12 depicts a flow diagram illustrating a methodology according to one or more embodiments of the invention.

DETAILED DESCRIPTION

Figure 1:
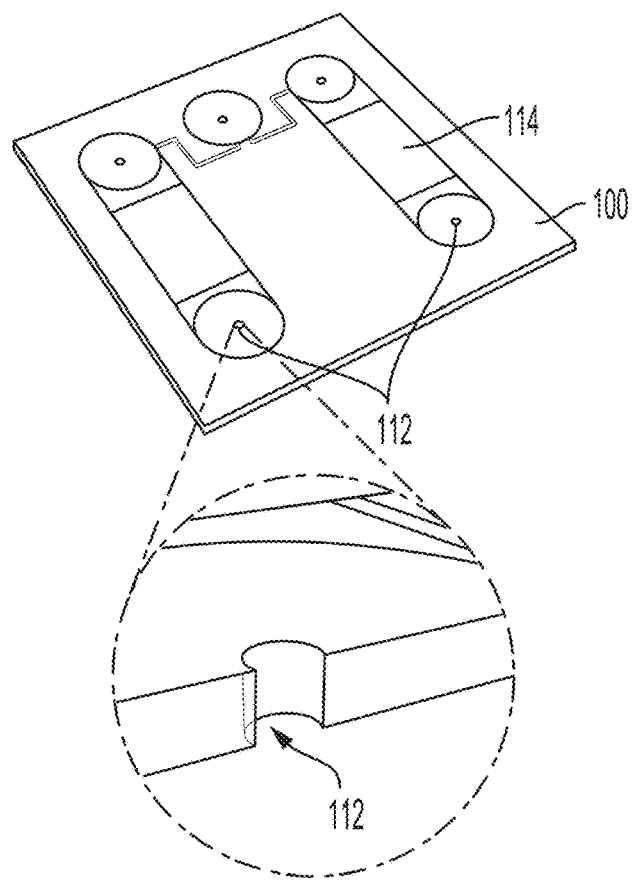
FIG. 1 depicts a nanofluidic device chip that has a network of nanofluidic channels and through-wafer vias according to one or more embodiments of the present invention.

Nanofluidics is a field of nanotechnology and engineering that manipulates fluids using nanofluidic devices having the critical structure dimensions that are on the order of nanometers. The importance of nanofluidic devices stems from their ability to manipulate samples in minute quantities, allowing the miniaturization of analytical and preparative methods that are normally carried out on the milliliter or greater scale. Many important biological, chemical, and material entities, such as proteins, organelles, plastids, supramolecular complexes, and colloids, function in fluids, and their manipulation and analysis can be facilitated with nanofluidic devices that are configured to handle small sample sizes.

The application of silicon (Si) nanofabrication to the field of biotechnology is opening opportunities in producing nanoscale fluidic devices. With the ability to produce small element features in high densities and at manufacturable volumes, silicon-based nanofluidics allows integration of biochemical and molecular biological techniques with on-chip sensors and logic. This integration of miniaturized biological techniques into lab-on-a-chip technology allows merging of sophisticated diagnostics with high mobility for broad applications in medicine, agriculture, manufacturing, and environmental monitoring.

In nanofluidic applications based on Si nanofabrication, a particular engineering aspect is the interfacing of the on-chip nanofluidic device and either (1) the external environment (macroscopic world) or (2) other on-chip components such as sensors, logic, reservoirs, etc. Fluidic samples can be loaded into the chip, and auxiliary fluids such as buffers, cleaning agents, reagents, etc. are metered out and injected into the fluid flow at desired intervals.

In addition, for practical applications, nanofluidic chips can be insulated from the external environment to prevent damage and contamination, and this requires a module for both housing the chip and allowing the various inputs and outputs to be connected to the chip in a secure, functional, and reproducible manner.

One of the challenges faced by known nanofluidic devices is low through-put between nanofluidic components or nanofluidic devices. Embodiments of the present invention are configured to address one or more of the above-described issues.

Embodiments of the present invention overcome the inherent low flux of nanofluidic systems and provide an economic and simple method for securing nanofluidic devices in parallel to receive and distribute a single sample fluid input. Embodiments of the present invention are capable of producing high throughput, for example, 1 ml/hour, by bonding multiple nanofluidic device chips into a single stack.

Traditionally, multi-layer chip stacks are prepared using polymer gaskets located between the chip layers. Such configuration provides a tight fluidic seal, but leaves a gap between stack layers, and does not provide a strong silicon-silicon bond. Such fluidic stacks could be suitable for cooling electronics, but they are not suitable for biomedical or chemical analysis applications.

In contrast to the traditional methods, embodiments of the present invention provide a method for increasing the flow output of nanofluidic devices by careful design and bonding of multiple chips without any gaskets or adhesive. Embodiments of the present invention use direct silicon-to-silicon or silicon-to-oxide bonding. Further, embodiments of the present invention enable sealing of the entire fluidic network at once thereby avoiding entry of any unwanted liquid or contaminant into the fluidic network.

Furthermore, embodiments of the present invention provide a number of advantages including the ability to increase the flow rate of a nanofluidic network from 10 s nL/hr up to mL/hr (a quantity range suitable for clinical and research applications); precise interfacing between nanostructured fluidic devices and macroscopic preparative facilities; the ability to produce a vertically integrated nanofluidic network by bonding nanofluidic device chips from a single wafer (thus avoiding the complex multi-tier microfabrication techniques); the ability to build modular nanofluidic systems where different fluidic networks can be "plumbed" (connected) in parallel by bonding different chip architectures into the stack; simple and flexible bonding method; and the ability to vary the flow capacity of a stack module by controlling the number of chips in the stack.

FIG. 1 shows a schematic of an exemplary nanofluidic device chip 100 having a network of nanofluidic channels 114. As shown in an expanded view of a portion of the device chip 100, the nanofluidic device chip 100 also includes a through-wafer via 112. The through-wafer via 112 is structured to allow a fluid connection between the nanofluidic device chip 100 and the outside fluid circuit (or another nanofluidic device chip 100). The design of the nanofluidic device chip 100 is such that all input and output fluid streams enter and leave through the through-wafer via 112.

Figure 2:
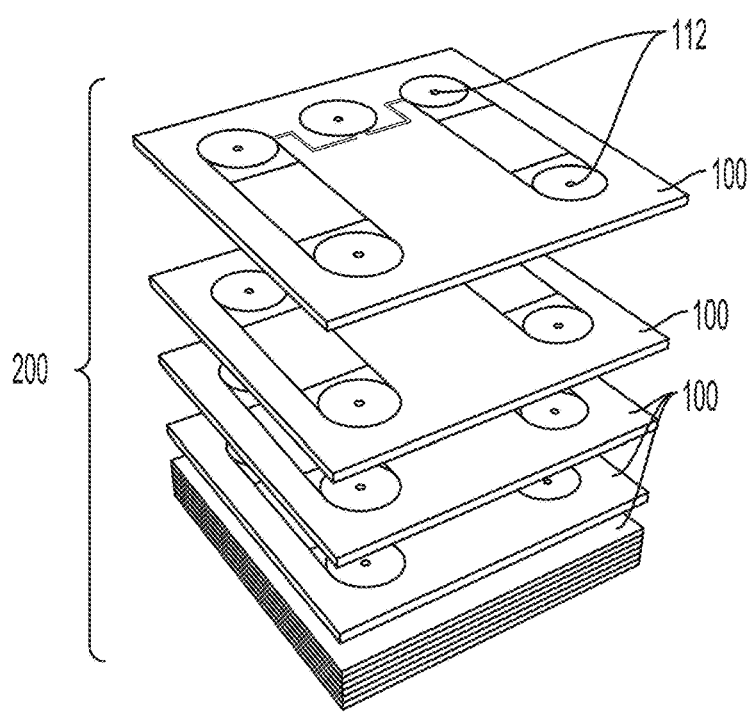
FIG. 2 depicts a stack of nanofluidic device chips where the nanofluidic device chips are arranged one on top of another according to one or more embodiments of the present invention.

FIG. 2 shows a stack 200 of nanofluidic device chips 100 arranged one on top of another. As shown in FIG. 2, the stack 200 is structured in a manner that the vias 112 of individual nanofluidic device chips 100 are aligned in a substantially straight line. The vias 112 allow interlayer fluid connection between the nanofluidic device chips 100 of the stack 200.

Figure 3A:
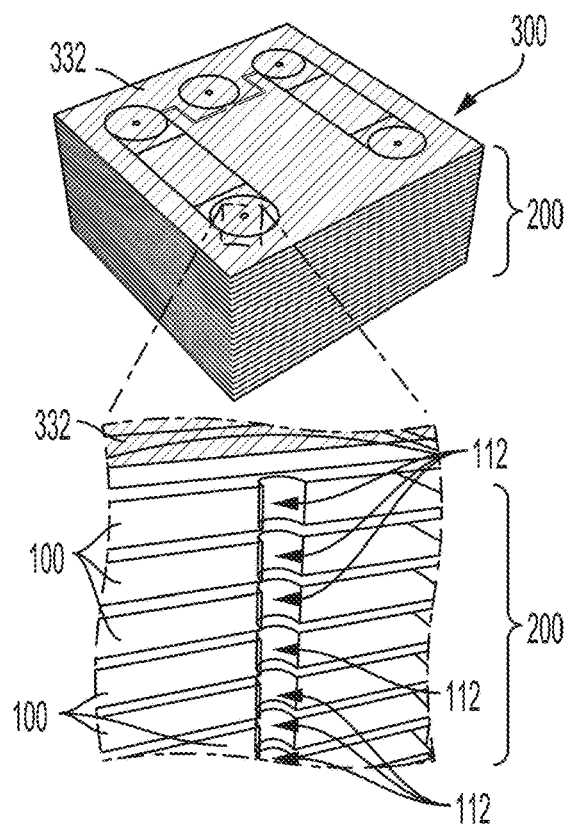
FIG. 3A depicts a stack of bonded nanofluidic device chips where a glass coverslip is deposited on top according to one or more embodiments of the present invention.

FIG. 3A shows a bonded chip stack 300 according to one or more embodiments of the present invention. The bonded chip stack 300 includes a stack 200 of nanofluidic device chips 100 arranged one on top of another, and bonded to each other. The vias 112 of individual nanofluidic device chips 100 are aligned in a straight line. A glass coverslip 332 is bonded to the top layer (i.e. top nanofluidic device chip 100) of the stack 200. The combined structure including the stack 200 and the glass coverslip 332 is referred as the bonded chip stack 300.

As shown in FIG. 3A, the nanofluidic device chips 100 are so arranged that fluids enter (input) and exit (output) the bonded chip stack 300 only from the bottom of the bonded chip stack 300. Fluids can reach to each layer (i.e. nanofluidic device chips 100) of the stack 200 through vias 112.

Figure 3B:
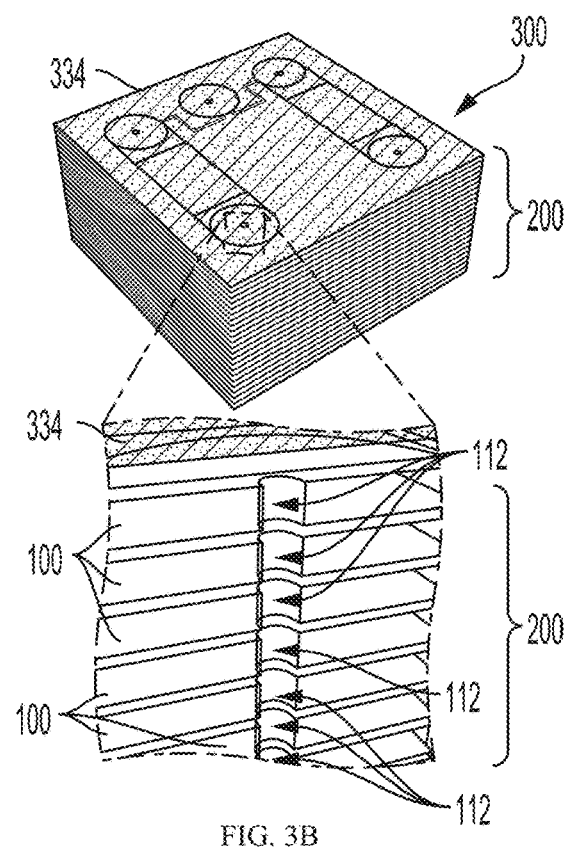
FIG. 3B depicts a stack of bonded nanofluidic device chips where a silicon cap is deposited on top according to one or more embodiments of the present invention.

FIG. 3B shows a bonded chip stack 300A according to one or more embodiments of the invention. The bonded chip stack 300A is substantially the same as the bonded chip stack 300 (shown in FIG. 3A) except that in the bonded chip stack 300A a silicon cap 334 is used in place of the glass coverslip 332 used in the bonded chip stack 300.

One of more embodiments of the method of producing the bonded chip stack 300 are explained below with reference to FIGS. 4-7.

Nanofluidic device chips 100 (as shown in FIG. 1) are fabricated using silicon nanofabrication methods. The nanofluidic device chips 100 are stripped of protective resist layers and cleaned to remove organic contaminates. The removal of protective resist layer depends on the protective resist layer chemistry, but typically requires a thorough rinsing in an organic solvent. Suitable organic solvents include electronics grade acetone, ethanol, and isopropanol.

The nanofluidic device chips 100 are further cleaned using an aqueous solution of a detergent. Typically, 1% (volume/volume) aqueous solution of detergent is used. The detergent cleaning is typically carried out by subjecting the chips 100 to boiling aqueous detergent solution for 20 to 30 minutes. Suitable detergents include non-ionic polyethyleneoxide polymers and derivatives, ionic detergents, electronics grade surfactants, and mixtures thereof. Suitable detergents also include TWEEN® 20, Pluronic® detergents, Micro-90® surfactant, and combinations thereof.

The nanofluidic device chips 100 are rinsed to remove any residual detergent by sequentially soaking in boiling deionized water for 20 to 30 minutes, for at least two times.

The surfaces of the nanofluidic device chips 100 are activated for bonding by submersing the chips in an activation solution at a suitable temperature for a suitable time. In one or more embodiments of the invention, the activation solution is 1:1 (v/v) mixture of sulfuric acid and hydrogen peroxide. In one or more embodiments of the invention, the activation solution is 1:1 (v/v) sulfuric acid:30% v hydrogen peroxide solution. In one or more embodiments of the invention, the activation solution is at a temperature in the range of about 60 to about 120° C. In one or more embodiments of the invention, the activation solution is at a temperature in the range of about 80° C. to about 100° C. In one or more embodiments of the invention, the activation solution is at a temperature of about 90° C. The submersing can be carried out for a period of about 30 to about 120 minutes. In one or more embodiments of the invention, the submersing is carried out for about 60 minutes at about 90° C. Chips 100 are further cleaned rapidly with deionized water and dried under a gas jet stream, such as purified and filtered nitrogen gas.

Figure 4:
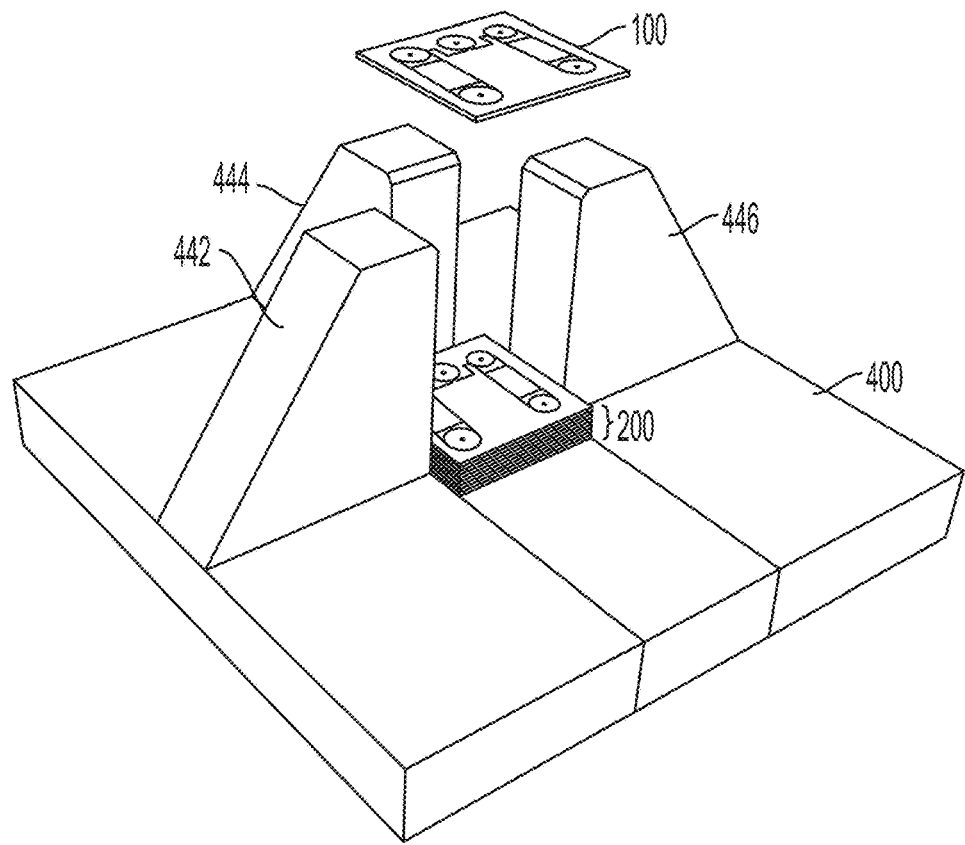
FIG. 4 depicts an alignment jig arranging and holding a stack of nanofluidic device chips according to one or more embodiments of the present invention.

As shown in FIG. 4, the activated chips 100 are arranged in a stack 200 by sequentially depositing individual chip 100 into an alignment jig 400. The alignment jig 400 includes walls 442, 444, and 446 configured to create a pocket that guides and aligns the chips 100 as they are added to the stack 200. The walls 442, 444, and 446 are machined to 0.001" tolerance and provide alignment accuracy of about 50-about 100 μm.

The walls 442, 444, 446 can be made mobile, such that they retract to allow chips to position over the stack, and then extended back to correct and guide alignment. The positioning of the chips 100 can be done manually by hand, or with the help of an automated robotic arm. Alignment is carried out in a clean environment to prevent dust particles incorporating between layers and causing bonding defects.

After each device chip 100 is added into the stack 200, pressure of 100-500 psi is applied for about 60 sec to ensure maximum contact between adjacent chip surfaces. The sequential assembly of the stack 200 is continued until a stack of required number of chip layers is constructed. The stack is then capped with either a glass coverslip 332 or a silicon cap 334 (blank silicon wafer) to seal the fluid circuit. The stack 200 together with glass coverslip 332 or silicon cap 334 is referred as stack 300.

Figure 5:
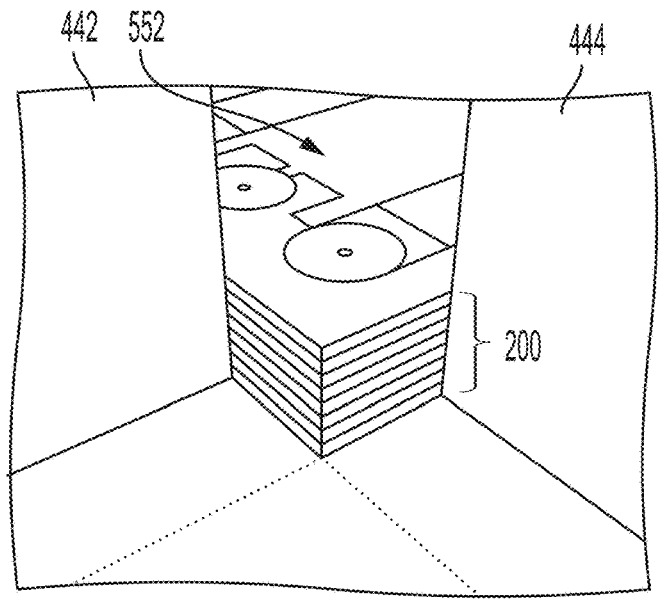
FIG. 5 depicts an expanded side-view of the alignment jig shown in FIG. 4 and illustrates mechanical pocketing of the nanofluidic device chips according to one or more embodiments of the present invention.

FIG. 5 illustrates the mechanical pocketing process. As shown in FIG. 5, the walls 442 and 444 forms a pocket 552 for building the stack 200.

Figure 6:
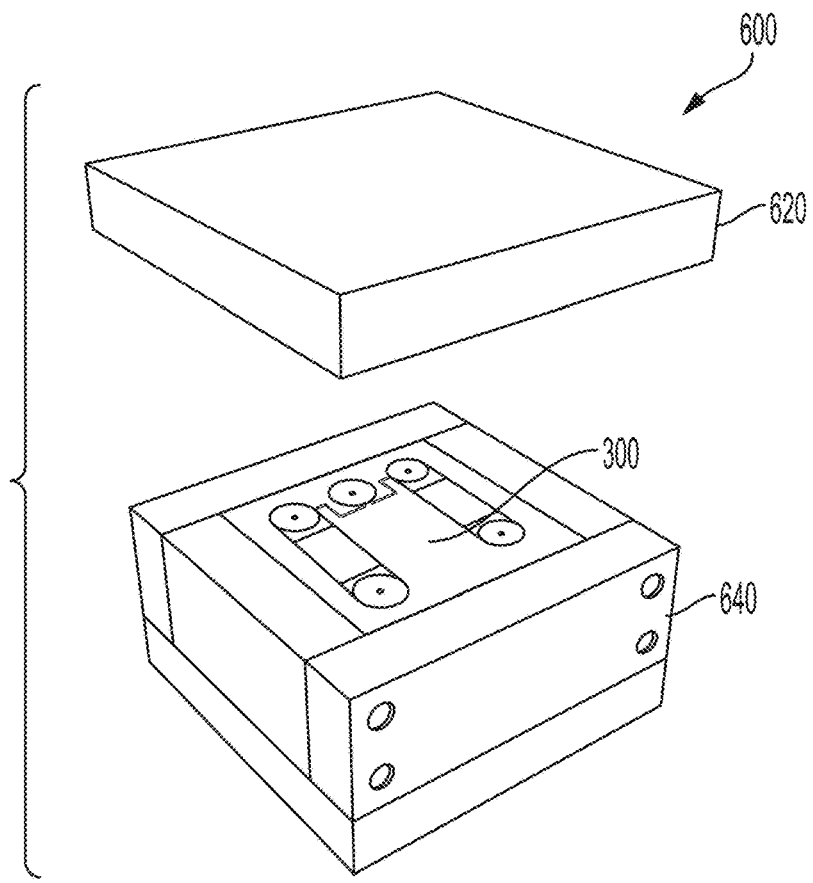
FIG. 6 depicts a three-dimensional exploded view of an annealing box containing a stack of nanofluidic device chips and a glass coverslip according to one or more embodiments of the present invention.
Figure 7:
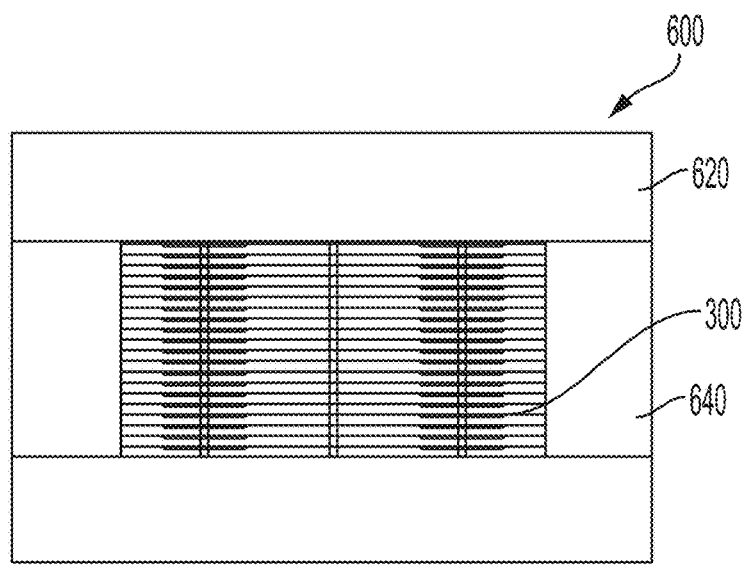
FIG. 7 depicts a cross-sectional unexploded view of the annealing box shown in FIG. 6 according to one or more embodiments of the present invention.

As shown in FIG. 6, the stack 300 is transferred to an annealing box 600. The annealing box 600 includes a lid 620 and an enclosing chamber 640. The enclosing chamber 640 of the annealing box 600 receives and holds the stack 300. The stack 300 is transferred to the annealing box 600 by disassembling the jig, and either manually transferring the stack 300 to the annealing box 600, or assembling the annealing box 600 around the stack 300. FIG. 7 depicts a cross-sectional unexploded view of the annealing box shown in FIG. 6 according to one or more embodiments of the present invention. FIG. 7 illustrates arrangement of the stack 300 inside the annealing box 300.

The enclosing chamber 640 of the annealing box 600 is constructed of a material that has a coefficient of thermal expansion (CTE) lower than the chip stack 300. In one or more embodiments of the invention, the enclosing chamber 640 is constructed of Invar metal. In one or more embodiments of the invention, the enclosing chamber 640 is constructed of a material selected from the group consisting of invar metal, invar alloy, alloy or ceramic material having low coefficient of thermal expansion, and combinations thereof. The dimensions of the enclosing chamber 640 are designed such that expansion of the chip stack 300 is larger than the expansion of the enclosing chamber 640 itself, leading to a compressive force being exerted on the chip stack 300 during the annealing process. The compressive force is chosen to be about ~10% the modulus of the silicon wafers, and the box dimensions are set so that full compression is achieved at the maximum annealing temperature. The maximum annealing temperature is about 550 to about 600° C. for a chip stack 300 including a glass coverslip 332. The maximum annealing temperature is about 600° C. to 1300° C. for a chip stack 300 including a silicon cap 334, with the preferred range being about 600° C. to 1000° C.

Figure 8:
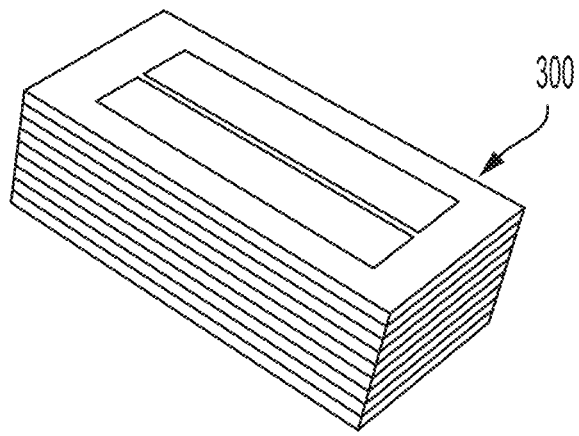
FIG. 8 depicts a bonded stack of nanofluidic device chips according to one or more embodiments of the present invention.
Figure 9:
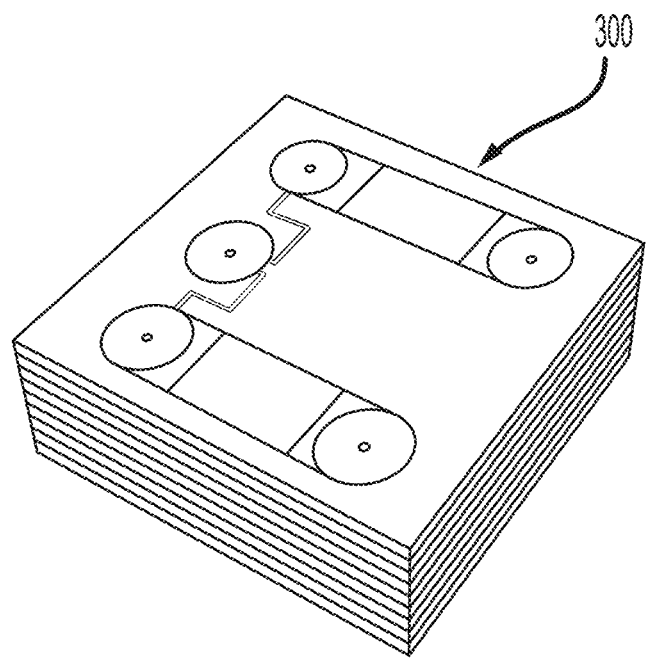
FIG. 9 depicts a bonded stack of nanofluidic device chips according to one or more embodiments of the present invention.

Chip stack 300 is annealed in an inert gas flow (e.g. nitrogen) for 8 hours at a specified temperature to allow heating and compression of the chip layers to form a fluid tight bond. FIG. 8 and FIG. 9 show chip stacks 300 after annealing.

The heating and cooling ramp rate is controlled so that the chip stack does not delaminate due to heat shock, and so that the box 600 does not damage the chip stack 300. The rate must be determined empirically based on design of the box 600. In one or more embodiments of the invention, a conservative heating/cooling rate of 1° C./min is applied.

In one or more embodiments of the invention, an alternative method is used to produce the bonded chip stack 300. In the alternative method embodiments, anodic bonding is used. The anodic bonding can be used in cases where simple pressure/temperature annealing is not sufficient to bond the nanofluidic device chips 100 (shown in FIG. 1). One or more embodiments according to the alternative method are described below.

Nanofluidic device chips 100 are fabricated using Si nanofabrication method. As shown in FIG. 1, each nanofluidic device chip 100 includes a nanofluidic network 114 and through-wafer vias 112. The actual design of the nanofluidic network can vary depending on the intended application of the nanofluidic device chip 100. However, the nanofluidic device chip 100 in accordance with aspects of the invention includes at least one through-wafer via 112.

Figure 10:
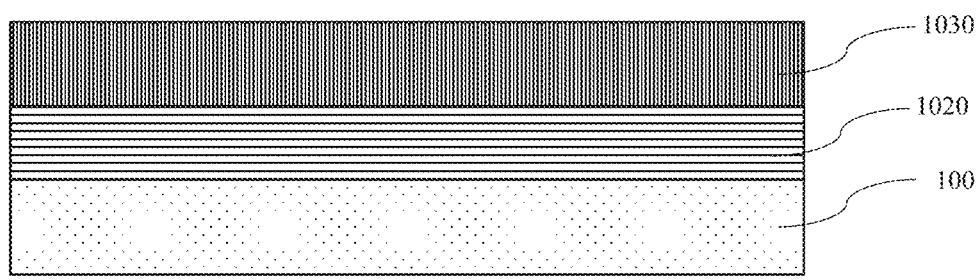
FIG. 10 depicts a side view of a nanofluidic device chip including a silicon oxide layer and a boron layer according to one or more embodiments of the present invention.

As shown in FIG. 10, a thin layer 1020 of silicon oxide is grown on the surface of each nanofluidic device chip 10. The silicon oxide layer 1020 can be 5-50 nm thick. The silicon oxide layer 1020 is implanted with a surface layer 1030 of boron on either the top or bottom side of the nanofluidic device chip 100. In one or more embodiments of the invention, the boron layer 1030 is formed only on one side of the chip 100 in order to provide a mobile cation defect population for effecting anodic bonding. This boron implantation must be conducted such that no further layers are processed on top of this ion layer, and with minimal annealing to prevent ion diffusion.

The nanofluidic device chips 100 are stripped of protective resist layers and cleaned to remove organic contaminates. The removal of protective resist layer depends on the protective resist layer chemistry, but typically requires a thorough rinsing in an organic solvent. Suitable organic solvents include electronics grade acetone, ethanol, and isopropanol.

The chips 100 are further cleaned using a detergent in an aqueous solution. Typically, a 1% (v/v) aqueous solution of detergent is used. The detergent cleaning is typically carried out by subjecting the chips 100 to boiling aqueous detergent solution for 20 to 30 minutes. Suitable detergents include non-ionic polyethyleneoxide polymers and derivatives, ionic detergents, electronics grade surfactants, and mixtures thereof. Suitable detergents also include TWEEN® 20, Pluronic® detergents, Micro-90® surfactant, and combinations thereof.

Chips 100 are rinsed of any residual detergent by sequential soaking in boiling deionized water for 20 to 30 minutes, for at least two times.

As shown in FIG. 4, the chips 100 are then arranged into a stack 200 by sequentially depositing individual chip 100 into an alignment jig 400. The alignment jig 400 includes walls 442, 444, and 446. The walls 442, 444, and 446 create a pocket that guides and aligns the chips as they are added to the growing stack 200. The walls 442, 444, and 446 are machined to 0.001" tolerance and provide alignment accuracy of 50-100 µm.

The walls 442, 444, 446 can be made mobile, such that they retract to allow chips to position over the stack, and then extended back to correct and guide alignment. The positioning of the chips 100 can be done manually by hand, or with the help of an automated robotic arm. Alignment is carried out in a clean environment to prevent dust particles incorporating between layers and causing bonding defects.

Electrical contacts are made to the bottom and top of the chip stack 200. The jig 400 is isolated such that there is no short-circuit between the top and bottom electrical contacts. The jig 400 applies a slight pressure (about 100 psi) to hold the stack 200 in place and preserve alignment of the stack 200.

The stack 200 is heated slowly to 400° C. In one or more embodiments of the invention, stack is heated to a temperature in the range of about 350° C. to about 450° C. An electric voltage of 100-500 VDC (Volt Direct Current) is applied to the stack 200. The ion current can be measured (in mA) to follow the procession of the anodic bonding. The ion current starts high and then slowly decays down to the µA range and remains steady, indicating that the bonding is complete. The applied voltage and run time depend on the number of layers in the stack 200. Typically, the applied voltage is in the range of 100-500 VDC applied for a period of about 40 to about 90 min.

Once the bonding is complete, the voltage is turned off and the stack 200 is allowed to cool slowly. The stack 200 can be further transferred to the annealing box 600 and the annealing procedure described above is carried out to obtain a bonded chip stack 300.

FIG. 11 depicts a flow diagram illustrating a methodology 1100 according to one or more embodiments of the present invention. At block 1102, nanofluidic device chips 100 are fabricated using silicon nanofabrication methods. At block 1104, the device chips 100 are rinsed with an organic solvent. At block 1106, the chips 100 are washed with an aqueous detergent solution. At block 1108, the chips 100 are rinsed with deionized water. At block 1110, the surfaces of the chips 100 are activated by submersing the chips 100 in an activating solution. At block 1112, the chips 100 are placed one on top of another using an alignment jig 400 to form stack 200. At block 1114, the stack 200 is subjected to annealing conditions.

FIG. 12 depicts a flow diagram illustrating a methodology 1200 according to one or more embodiments of the present invention. At block 1202, nanofluidic device chips 100 are fabricated using silicon nanofabrication methods. At block 1204, a layer of silicon oxide 1020 is formed on surfaces of chips 100. At block 1206, a boron layer 1030 is implanted on the silicon oxide layer 1020. At block 1208, the chips 100 are washed with an aqueous detergent solution. At block 1210, the chips 100 are placed one on top of another using an alignment jig 400 to form stack 200. At block 1214, electric voltage is applied to the stack 200 to form anodic bonding.

It will be noted that various microelectronic device fabrication methods can be utilized to fabricate the components/elements (for example, nanofluidic device chip 100) discussed herein as understood by one skilled in the art. In semiconductor device fabrication, the various processing steps fall into four general categories: deposition, removal, patterning, and modification of electrical properties.

Deposition is any process that grows, coats, or otherwise transfers a material onto the wafer. Available technologies include physical vapor deposition (PVD), chemical vapor deposition (CVD), electrochemical deposition (ECD), molecular beam epitaxy (MBE) and more recently, atomic layer deposition (ALD) among others.

Removal is any process that removes material from the wafer: examples include etch processes (either wet or dry), and chemical-mechanical planarization (CMP), etc.

Patterning is the shaping or altering of deposited materials, and is generally referred to as lithography. For example, in conventional lithography, the wafer is coated with a chemical called a photoresist; then, a machine called a stepper focuses, aligns, and moves a mask, exposing select portions of the wafer below to short wavelength light; the exposed regions are washed away by a developer solution. After etching or other processing, the remaining photoresist is removed. Patterning also includes electron-beam lithography.

Modification of electrical properties can include doping, such as doping transistor sources and drains, generally by diffusion and/or by ion implantation. These doping processes are followed by furnace annealing or by rapid thermal annealing (RTA). Annealing serves to activate the implanted dopants.

The terms "about," "substantially," "approximately," "slightly less than," and variations thereof, are intended to include the degree of error associated with measurement of the particular quantity based upon the equipment available at the time of filing the application. For example, "about" can include a range of ±8% or 5%, or 2% of a given value.

The flowchart and block diagrams in the Figures illustrate the architecture, functionality, and operation of possible implementations of systems, methods, and computer program products according to various embodiments of the present invention. In this regard, each block in the flowchart or block diagrams can represent a module, segment, or portion of instructions, which includes one or more executable instructions for implementing the specified logical function(s). In some alternative implementations, the functions noted in the block can occur out of the order noted in the figures. For example, two blocks shown in succession can, in fact, be executed substantially concurrently, or the blocks can sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A method of forming a bonded chip stack, the method comprising: forming a first nanofluidic device chip having a first through-wafer via;
   forming a second nanofluidic device chip having a second through-wafer via;
   washing the first nanofluidic device chip and the second nanofluidic device chip with a detergent solution;
   activating a first surface of the first nanofluidic device chip and a second surface of the second nanofluidic device chip by treating the first surface and the second surface with an activation solution;
   arranging the first nanofluidic device chip and the second nanofluidic device chip in a stack, wherein the first through-wafer via is aligned with the second through wafer via in a substantially straight line; and
   subjecting the stack of first and second nanofluidic device chips to annealing conditions.

2. The method of claim 1 further comprising depositing a glass coverslip or a silicon cap layer on top of the stack of the nanofluidic device chips.

3. The method of claim 1, wherein the washing is carried out by subjecting the nanofluidic device chips to the detergent solution at its boiling point for a period of 20 to 30 minutes.

4. The method of claim 3, wherein the detergent solution comprises an about 1% volume/volume aqueous detergent solution.

5. The method of claim 4, wherein the detergent is selected from a group consisting of non-ionic polyethyleneoxide polymers and derivatives, ionic detergents, electronics grade surfactants, and mixtures thereof.

6. The method of claim 1, wherein the activation solution is selected from a group consisting of:
   1:1 volume/volume solution of sulfuric acid and 30% (v/v) hydrogen peroxide; and
   oxygen or ozone plasma or a rapid wash with a strong alkaline solution.

7. The method of claim 6, wherein the activating comprises subjecting the nanofluidic device chips to the activation solution at a temperature of about 80° C. to about 100° C. for about 40 to about 80 minutes.

8. The method of claim 1, wherein:
   the arranging is carried out in an alignment jig comprising at least three walls; and
   the alignment jig has alignment accuracy of about 50 to about 100 μm.

9. The method of claim 8, wherein the arranging comprises sequentially depositing the nanofluidic device chips into a mechanical pocket formed by walls of the alignment jigs.

10. The method of claim 9 further comprising applying a pressure of about 100-500 psi to the stack after addition of each of the first and second nanofluidic device chips.

11. The method of claim 1 further comprising depositing a glass coverslip or a silicon cap on top of the stack prior to subjecting the stack to the annealing conditions.

12. The method of claim 11, wherein:
   the stack comprises the glass coverslip; and
   the annealing conditions comprise a maximum annealing temperature of about 550° C. to 600° C.

13. The method of claim 11, wherein:
   the stack comprises the silicon cap; and
   the annealing conditions comprise a maximum annealing temperature of about 600-1000° C.

14. The method of claim 1, wherein the annealing is carried out in an annealing box comprising a material having coefficient of thermal expansion less than that of silicon.

15. The method of claim 14, wherein the annealing box comprises a material selected from a group consisting of invar metal, invar alloy, alloy, ceramic material having low coefficient of thermal expansion, and combinations thereof.

16. A method of producing a bonded chip stack, the method comprising:
   providing at least two nanofluidic device chips wherein each nanofluidic device chip comprises at least one through wafer via;
   forming a silicon oxide layer on the surface of each of the at least two nanofluidic device chips;
   implanting a boron layer on the silicon oxide layer;
   washing the nanofluidic device chips with a detergent solution;
   arranging the nanofluidic device chips in a stack wherein the at least one through wafer via of each nanofluidic device chip is aligned in a straight line;
   applying an electrical voltage to the stack of nanofluidic device chips.

17. The method of claim 16 further comprising subjecting the stack of first and second nanofluidic device chips to annealing conditions.

18. The method of claim 16 further comprising heating the stack of first and second nanofluidic device chips to a temperature of about 350° C. to about 450° C. prior to applying the electric voltage.

19. The method of claim 16, wherein the electric voltage comprises 100-500 volt direct current, and the voltage is applied for a period of 40 to 90 minutes.

* * * * *